US010067075B2

(12) United States Patent
Torun et al.

(10) Patent No.: US 10,067,075 B2
(45) Date of Patent: Sep. 4, 2018

(54) BIOSENSOR WITH INTEGRATED ANTENNA AND MEASUREMENT METHOD FOR BIOSENSING APPLICATIONS

(71) Applicant: BOGAZICI UNIVERSITESI, Istanbul (TR)

(72) Inventors: Hamdi Torun, Istanbul (TR); Arda Deniz Yalcinkaya, Istanbul (TR); Gunhan Dundar, Istanbul (TR)

(73) Assignee: BOGAZICI UNIVERSITESI, Istanbul (TR)

( * ) Notice: Subject to any disclaimer, the term of this patent is extended or adjusted under 35 U.S.C. 154(b) by 0 days.

(21) Appl. No.: 15/511,647

(22) PCT Filed: Sep. 14, 2015

(86) PCT No.: PCT/TR2015/050101
§ 371 (c)(1),
(2) Date: Mar. 16, 2017

(87) PCT Pub. No.: WO2016/048257
PCT Pub. Date: Mar. 31, 2016

(65) Prior Publication Data
US 2017/0292920 A1    Oct. 12, 2017

(30) Foreign Application Priority Data
Sep. 24, 2014    (TR) ................ 2014 11254

(51) Int. Cl.
*H01P 11/00*    (2006.01)
*H01P 7/00*    (2006.01)
(Continued)

(52) U.S. Cl.
CPC ............. *G01N 22/00* (2013.01); *H01Q 1/225* (2013.01); *H01Q 9/0464* (2013.01); *H01Q 9/40* (2013.01)

(58) Field of Classification Search
CPC ...... G01N 22/00; H01Q 1/225; H01Q 9/0464; H01Q 9/40
See application file for complete search history.

(56) References Cited

U.S. PATENT DOCUMENTS 7,564,244 B2 *    7/2009    Freytag ............ G01R 33/34007
                                                                324/309
7,964,144 B1    6/2011    Nordin et al.
(Continued)

FOREIGN PATENT DOCUMENTS

EP    1911206 A1    4/2008
EP    1912062 A1    4/2008
(Continued)

OTHER PUBLICATIONS

Abduljabar, Ali A., et al. "Novel microwave microfluidic sensor using a microstrip split-ring resonator." IEEE Transactions on Microwave Theory and Techniques 62.3 (2014): 679-688.*
(Continued)

*Primary Examiner* — Robert Eom
(74) *Attorney, Agent, or Firm* — Gokalp Bayramoglu (57) ABSTRACT

The present invention relates to a biosensor (1) which enables the concentration of a desired molecule inside a liquid in the medium, and essentially comprises at least one metallic plate (2) which functions as a ground plate, and which is preferably manufactured from aluminum, at least one dielectric substrate (3) which is located on top of the metallic plate (2), at least one split-ring resonator (4) which is realized on top of the dielectric substrate (3), and which is coated with a dielectric layer, at least two symmetrical antennas (5) which are realized on the same plane with the split-ring resonator (4) on the substrate (3), at least two ports (6) where a network analyzer is connected with the antennas (5) via SMA (SubMiniature Version A) connectors.

2 Claims, 4 Drawing Sheets

(51) Int. Cl.
*H01P 7/08* (2006.01)
*H01P 7/10* (2006.01)
*G01N 29/00* (2006.01)
*G01N 29/036* (2006.01)
*G01N 22/00* (2006.01)
*H01Q 1/22* (2006.01)
*H01Q 9/04* (2006.01)
*H01Q 9/40* (2006.01)

(56) References Cited

U.S. PATENT DOCUMENTS

| | | | |
|---|---|---|---|
| 2011/0012477 A1 | 1/2011 | Chommeloux et al. | |
| 2011/0152725 A1 | 6/2011 | Demir et al. | |
| 2011/0287218 A1* | 11/2011 | Narimanov | G02B 1/002 |
| | | | 428/141 |

FOREIGN PATENT DOCUMENTS

| | | |
|---|---|---|
| KR | 20140079094 A | 6/2014 |
| WO | WO2010028077 A1 | 3/2010 |

OTHER PUBLICATIONS

Torun, H., et al. "An antenna-coupled split-ring resonator for biosensing." Journal of Applied Physics 116.12 (2014): 124701.*

Aydin, Koray, et al. "Investigation of magnetic resonances for different split-ring resonator parameters and designs." New journal of physics 7.1 (2005): 168.*

Lee Hee-Jo et al:"DNA sensing using split-ring resonator alone at microwave regime", Journal of Applied Physics, American Institute of Physics, US, vol. 108, No. 1, Jul. 14, 2010 (Jul. 14, 2010), pp. 14908-1-14908-6, XP012141834, ISSN: 0021-8979, DOI:10.1063/1.3459877 p. 1, right-hand column, paragraph II-p. 4, paragraph IV.

Ali Karami Horestani et al:"Displacement Sensor Based on Diamond-Shaped Tapered Split Ring Resonator", IEEE Sensors Journal, vol. 13, No. 4, Apr. 2013, pp. 1153-1160.

Irfan Bulu et al:"Compact size highly directive antennas based on the SRR metamaterial medium", New Journal of Physics, 7 (2005) 223, DOI:10.1088/1367-2630/7/1/223.

Saber Dakhli et al:"Efficient,Metamaterial-Inspired Loop-Monopole Antenna with Shaped Radiation Pattern", Loughborough Antennas & Propagation Conference, 2012.

Levent Sahin et al:"Enhanced transmission of electromagnetic waves through split-ring resonator-shaped apertures", Journal of Nanophotonics 051812-1 vol. 5, 2011, DOI: 10.1117/1.3599873.

Withawat Withayachumnankul et al:"Metamaterial-based microfluidic sensor for dielectric characterization", Sensors and Actuators A: Physical, 189(0), 233-237(2013).

Muhammed S. Boybay et al:"Microwave sensing and heating of individual droplets in microfluidic devices", Lab on a Chip, 13(19), 3840-3846(2013),DOI: 10.1039/c3lc50418b.

Hee-Jo Lee et al:"A planar split-ring resonator-based microwave biosensor for label-free detection of biomolecules", Sensors and Actuators B: Chemical 169(0), 26-31 (2012), DOI:10.1016/j.snb.2012.01.044.

Hee-Jo Lee et al:"Biosensing using split-ring resonators at microwave regime", Applied Physics Letters, 92 (25) (2008), DOI: 10.1063/1.2946656.

* cited by examiner

BIOSENSOR WITH INTEGRATED ANTENNA AND MEASUREMENT METHOD FOR BIOSENSING APPLICATIONS

CROSS REFERENCE

This application is the national phase of International Application No. PCT/TR2015/050101, filed on Sep. 14, 2015, which is based upon and claims priority to Turkish Patent Application No. 2014/11254, filed on Sep. 24, 2014, the entire contents of which are incorporated herein by reference.

TECHNICAL FIELD

The present invention relates to a sensor (BioSRR) operating in microwave frequencies. More specifically, a split-ring resonator with integrated antennas is disclosed. The said sensor can be used in field of detecting biomolecules.

BACKGROUND

Split-ring resonators (SRR) have been widely used for applications in electromagnetic spectrum spanning from microwave to photonic frequencies. SRR structure defines a basic inductance-capacitance (LC) resonator electrically. The resonant frequency of the resonator is determined with the geometry of the structure. The structures whose dimensions are measured by millimeter and centimeters are generally used for applications in microwave frequency. Structures in micrometer-scale are used for terahertz frequencies, while smaller structures in nanometer-scale work in infrared and the visible light spectrum. When SRR structures are excited appropriately, the magnetic permeability becomes negative within the vicinity of the resonant frequency of the structure. This property is used for developing extraordinary properties such as negative index of refraction.

Unlike other passive resonator tanks, SRR structures can exhibit sharp resonant behavior with quality factor 1000 and above in microwave frequencies. Thus, the changes in resonant frequency of SRR structures can be used as a very effective sensing mechanism. The strain sensors working on this basis have been demonstrated in the literature [1-6]. The changes in SRR geometry due to strain change the resonant frequency of the structure, and this change is measured. Further, the resonant frequency is sensitive to change in dielectric constant of the medium in which the structure is present. This property has also been used for microfluidic applications. The geometry of the structure does not change in these applications, however the changes in dielectric properties of the medium in which it is present result in changes in the effective capacitance of the SRR structure, therefore the resonant frequency of the structure shifts. Biosensors using this mechanism have also been developed. Biomolecules binding on the surface of SRR structures alters the dielectric constant of the structures. SRR structures used with microstrip lines have been demonstrated for applications of hormone and antigen detection. Similar structures have been used for measuring biotin-streptavidin interaction and DNA hybridization.

External antennas are used for electrical excitation of SRR structures in the state of the art. The alignment of these antennas imposes an important limitation to realize portable sensors. In addition, large external antennas are not suitable for integration with electronic chips.

The transmission (s21) characteristic (s21 spectrum) of SRR structures demonstrated in the current technique exhibits a sharp dip at resonance. The shift of this dip frequency can be measured with measurement equipment such as vector network analyzers. However, it is not advantageous to use the sensors exhibiting this electrical property as part of oscillators by integrating with electronic circuits.

Korean Patent Document No. KR20140079094 (A), an application known in the state of the art, discloses a resonator, the electrical parameters of which change under interaction with biomolecules and wherein the said change is measured with a measurement method used with the resonator. The measurement method, which requires direct electrical connection to the resonator structure is different from the inventive system. In the inventive biosensor, direct electrical connection to the resonator structure is not required; this structure is excited with electromagnetic waves. The antennas integrated to the resonator for excitation can be used with different measurement methods.

European Patent Document No. EP1912062 (A1), an application known in the state of the art, discloses a structure the electrical capacitance value of which can change. The said structure is comprised of electrodes defined on a dielectric substrate. The electrodes are coated with biomolecules, and the electrical capacitance of the structure changes due to interaction between biomolecules. The change in capacitance is detected using an electronic circuit which is used together with the electrodes. The said disclosed structures are different from the inventive biosensor in terms of both function and structure. Contrary to EP1911206 (A1) disclosing a capacitor, the inventive system suggests a new resonator structure. With the inventive BioSRR method, disclosed is a new resonator operating in microwave band, the surface of which can be coated with biomolecules, integrated with an antenna is disclosed. The said resonator is excited by means of the integrated antennas, and the resonance frequency shifts can be measured.

In the article published as "Displacement Sensor Based on Diamond-Shaped Tapered Split Ring Resonator", IEEE SENSORS JOURNAL, VOL. 13, NO. 4, APRIL 2013, blown in the state of the art, a sensor structure has been developed for measuring displacement information on the position and the structure. The structure is defined in a coplanar waveguide for the measurements. The electrical characteristics of the structure are measured by means of the said waveguide. The sensor disclosed in this article is different from the inventive BioSRR in terms of measurement method and the structure.

U.S. Pat. No. 7,964,144 (B1), a patent known in the state of the art, discloses a structure comprised of a pair of electrode structure defined on a substrate and AIN base structure defined in the middle of the electrodes. The electrodes are used to form a horizontal surface acoustic wave and to collect the formed wave. The said method is used for different applications in the field, and it is different from the resonator defined with the inventive BioSRR.

In the article published as "Compact size highly directive antennas based on the SRR metamaterial medium", *New Journal of Physics,* 7 (2005) 223 in the state of the art, split-ring resonator structures defined on FR4 substrate are disclosed. The frequency responses of these structures are measured by means of external monopole and horn antennas. Furthermore, these structures are placed inside the antennas, and directed wave propagation is achieved. The application disclosed in this article is completely different from the inventive BioSRR. Furthermore, the method used to excite the resonator structures in BioSRR method is based on defining the resonator and the antenna on a single substrate in an integrated manner. These antennas and the structure are excited with hybrid Tem mode wave. On the other hand, resonator and antenna structures in the BioSRR method are defined on top of a dielectric substrate that is attached to a metal backplate. The presence of this backplate results in the transmission (s21) and reflection (s11) characteristics observed in this article.

The structure disclosed in the article published as "Efficient, Metamaterial-Inspired Loop-Monopole Antenna with Shaped Radiation Pattern", 2012 Loughborough Antennas & Propagation Conference in the state of the art is a new antenna. The disclosed antenna is electrically loaded with a split-ring resonator, and improvements in transmission/reflection characteristic of the antenna are achieved. The application fields of the structure disclosed in this article and the inventive BioSRR structure are different from each other. BioSRR method does not suggest a new antenna structure. A pair of monopole patch antennas integrated to the resonator structure is used for measuring the resonator characteristic. Split-ring resonator is used as a sensor structure in BioSRR. Furthermore, resonator and antenna structures in the BioSRR method are defined on top of a dielectric substrate that is attached to a metal backplate. The presence of this backplate results in the transmission (s21) and reflection (s11) characteristics observed in this article.

In the article published as "Enhanced transmission of electromagnetic waves through split-ring resonator-shaped apertures", Journal of Nanophotonics 051812-1 Vol. 5, 2011 known in the state of the art, split-ring resonators are integrated to the waveguides, and used to increase the electromagnetic permeability of the guide. In this application, the electromagnetic wave propagates along with the normal of the resonator structure, so the incidence angle is 90°. The device disclosed in this article is completely different from the inventive BioSRR in terms of application structure and function. In BioSRR method, it is the antenna pair exciting the resonator, not the waveguide. The electromagnetic wave propagates perpendicular to the normal of the resonator, so the incidence angle is 0°.

United States Patent Application No. US20110152725A1, an application known in the state of the art, discloses a structure comprised of planar coil and split-ring resonators suggested for biological applications. These structures are especially used for displacement measurement. External antennas are used for the measurements. The said measurement method is different from the method of using an integrated pair of antennas with the resonator suggested in BioSRR. Furthermore, the resonator and antenna structures in the BioSRR method are defined on top of a dielectric substrate that is attached to a metal backplate. The presence of this backplate results in the transmission (s21) and reflection (s11) characteristics observed in this article.

REFERENCES

1. K. Horestani, C. Fumeaux, S. F. Al-Sarawi, and D. Abbott, Sensors Journal, IEEE 13 (4), 1153 (2013).
2. Withawat Withayachumnankul, Kata Jaruwongrungsee, Adisorn Tuantranont, Christophe Fumeaux, and Derek Abbott, Sensors and Actuators A: Physical 189 (0), 233 (2013).
3. Muhammed S. Boybay, Austin Jiao, Tomasz Glawdel, and Carolyn L. Ren, Lab on a Chip 13 (19), 3840 (2013).
4. Hee-Jo Lee, Jung-Hyun Lee, Hui-Sung Moon, Ik-Soon Jang, Jong-Soon Choi, Jong-Gwan Yook, and Hyo-Il Jung, Sensors and Actuators B: Chemical 169 (0), 26 (2012).
5. Hee-Jo Lee and Jong-Gwan Yook, Applied Physics Letters 92 (25) (2008).
6. Hee-Jo Lee, Hyun-Seok Lee, Kyung-Hwa Yoo, and Jong-Gwan Yook, Journal of Applied Physics 108 (1) (2010).

SUMMARY OF INVENTION

The objective of the present invention is to provide a biosensor wherein the antennas are manufactured on the same substrate with the split-ring resonators (SRR), and this structure is integrated with the electronic readout circuit. The inventive biosensor is excited by electromagnetic waves. The said electromagnetic wave is provided by means of the electric signal applied on the antennas that is converted into electromagnetic waves. The shift in resonant frequency of the resonator can be measured using the receiver antenna and the electronic readout circuit; therefore, the concentration of the molecules in the medium can be measured. By means of the wave moving towards the SRR being on the same axis with the antennas, a more efficient current can be induced in the SRR.

The biosensor design provides advantage relative to the previous inventions since it allows realizing a split-ring resonator on a dielectric substrate together with the integrated antennas.

The frequency of the peak formed in the electromagnetic transmission response (s21) of the biosensor forms the basis of the detection function. This characteristic originates from the connection of the integrated monopole antennas and the thick metallic layer present under the dielectric substrate with the split-ring resonator. This property can be exploited to realize an oscillator circuit using the resonator.

The aluminum backplate placed under the substrate of the split-ring resonator is a metal plate, and the reflection (s11) and transmission (s21) characteristics can be changed by means of this plate. By this means, the electronic oscillator circuits to which the resonators are integrated can be achieved.

BRIEF DESCRIPTION OF DRAWINGS

A biosensor developed to fulfill the objectives of the present invention is illustrated in the accompanying figures, in which.

The components shown in the figures are each given reference numbers as follows:
1. Biosensor
2. Metallic plate
3. Substrate
4. Split-ring resonator
5. Antenna 6. Port
F. FGF-2
H. Heparin
L. Water droplet
P. Parylene
K1. Location—1
K2. Location—2
K3. Location—3
K4. Location—4
N. Nominal
s11. Reflection
s21. Transmission

DETAILED DESCRIPTION OF INVENTION

A biosensor (1), which enables the concentration of a desired molecule inside a liquid in the medium, essentially comprises
- at least one metallic plate (2) which functions as a ground plate, and which is preferably manufactured from aluminum,
- at least one dielectric substrate (3) which is located on top of the metallic plate (2),
- at least one split-ring resonator (4) which is realized on the dielectric substrate (3), and which is coated with a dielectric layer,
- at least two symmetrical antennas (5) which are realized on the same plane with the split-ring resonator (4) on top of the substrate (3),
- at least two ports (6) where a network analyzer is connected to the antennas (5) via SMA (SubMiniature Version A) connectors.

Figure 1:
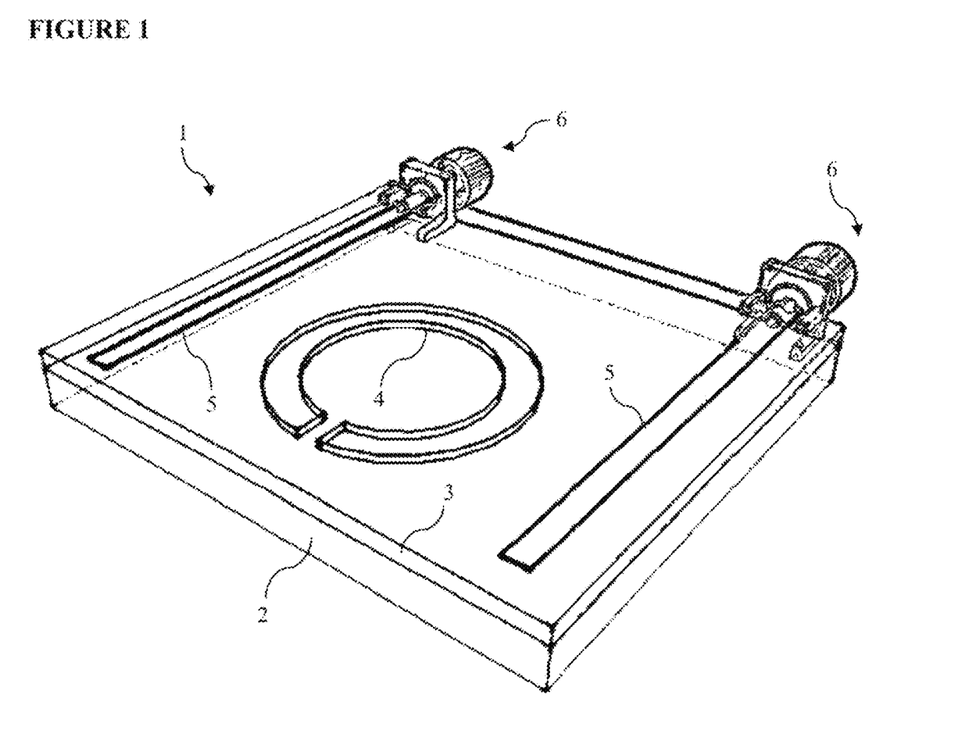
FIG. 1 is the perspective view of the inventive biosensor.

The three-dimensional schematic of the inventive biosensor (1) is shown in FIG. 1. The inventive biosensor (1) is comprised of a split-ring resonator (4) formed of split metallic ring realized on top of a dielectric substrate (3) and two symmetrical monopole antennas (5). The connection with the antennas (5) is achieved through ports (6) via the SMA (SubMiniature Version A) connectors. The dielectric substrate (3) is on a metallic plate (2) functioning as a ground plate and preferably manufactured from aluminum.

In a preferred embodiment of the invention, biosensor (1) is realized on a FR4 substrate (3) which is commonly used for printed circuit boards. In another embodiment of the invention, the substrate (3) of the biosensor (1) can also be manufactured on dielectric ceramics such as alumina, and mica. The fabrication of the biosensor (1) is realized with standard printed circuit board methods. After the definition of metallic structures on the FR4 substrate (3), there is a thin Parylene (P) material deposition process. Parylene (P) is a biocompatible material used for anchoring the biomolecules on the biosensor. The deposition process is performed at room temperature using chemical vapor deposition, and its geometric definition is performed using lithography and oxygen plasma etching. The resulting metallic structure behaves as a kind of LC resonator, and it can be excited with a magnetic field perpendicular to its own plane in a frequency known as magnetic resonance ($f_m$). Such excitation induces a current circulating around the ring. In accordance with the equivalent modelling with the lumped elements, the resonant frequency is given by the following equation:

$$f_m = \frac{1}{2\pi\sqrt{C_{eff}L_{eff}}}, \quad C_{eff} = C_g + C_s \quad \text{(Equation 1)}$$

$C_{eff}$ in this equation gives the efficient capacitance, and $L_{eff}$ gives efficient inductance; and these parameters are determined by the geometric design. Efficient capacitance is determined by two capacitance values which are parallel to each other. The first one of these is gap capacitance modeled with $C_g$, its value is given by the following equation:

$$C_g = \varepsilon_{eff}\frac{h\omega}{g} + \varepsilon_{eff}(h+g+w) \quad \text{(Equation 2)}$$

h, w and g in this equation is the thickness and width of the metallic structure, and the slit gap. Capacitance ($C_s$) is associated with the surface charges changes with r which is the radius of the ring, and its value is given by the following equation:

$$C_s = 2\varepsilon_{eff}\frac{(h+\omega)}{\pi}\ln\left(\frac{4r}{g}\right) \quad \text{(Equation 3)}$$

As it can be seen from equation 2 and equation 3, effective permittivity ($\varepsilon_{eff}$) of the media surrounding the split-ring resonator (4) is present as a multiplier in the surface and gap capacitances. In summary, a change in effective permittivity can shift the resonant frequency.

In order to measure the electromagnetic characteristics of the structure, a pair of identical monopole antennas (5) is realized in the sample plane with the split-ring resonator (4) symmetrically. The electromagnetic wave emitted from the antennas (5) is reflected from the aluminum plate (2) used as a ground plane and transmitted to the split-ring resonator (4). The emitted wave interacts with the split-ring resonator (4), and significantly increases the transmission (s21) in the vicinity of $f_m$ frequency which the resonant frequency of magnetic resonance. The said transmission (s21) characteristic was examined according to relative permittivity change, and the sensor applications were considered.

Figure 2A:
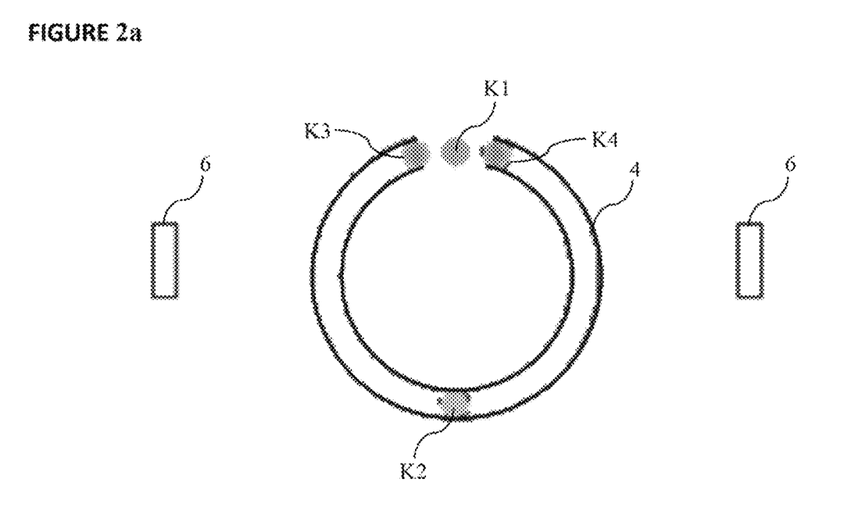
FIG. 2a is the schematic view showing the locations of deionized water droplets in volume of 16 µL on the metallic plate in one embodiment of the invention.

A prototype was manufactured in order to be used in biosensing applications. The details of the application are as follows:

The scattering circuit parameters of the biosensor (1) were measured by means of a vector network analyzer. In this process, both reflection (s11) and transmission (s21) parameters were characterized by using SMA connectors shown in FIG. 1. Reflection (s11) and transmission (s21) measurements were repeated by placing deionized water droplets (L) to different points of split-ring resonator (4) coated with a thin layer of Parylene (P). The volume of each water droplets (L) was measured as 16 µL with 2% precision. The location of the points on the split-ring resonator (4) at which the droplets are placed is shown in FIG. 2a. Deionized water droplets (L) increase the gap capacitance or surface capacitance according to their location on the split-ring resonator (4).

Figure 2B:
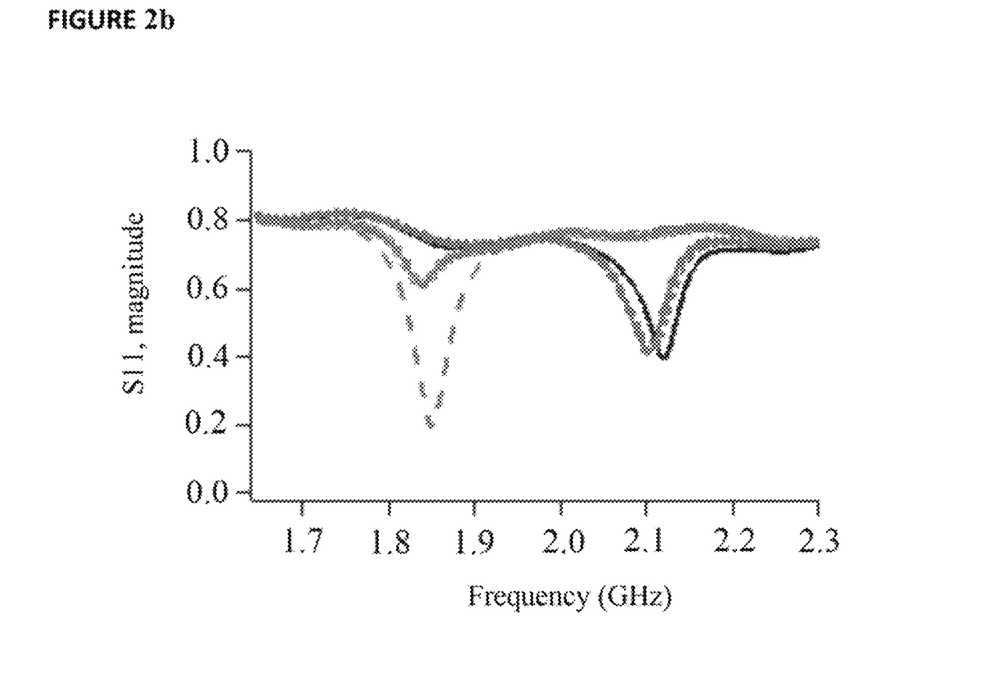
FIG. 2b is the measured reflection (s11) characteristic.
Figure 2C:
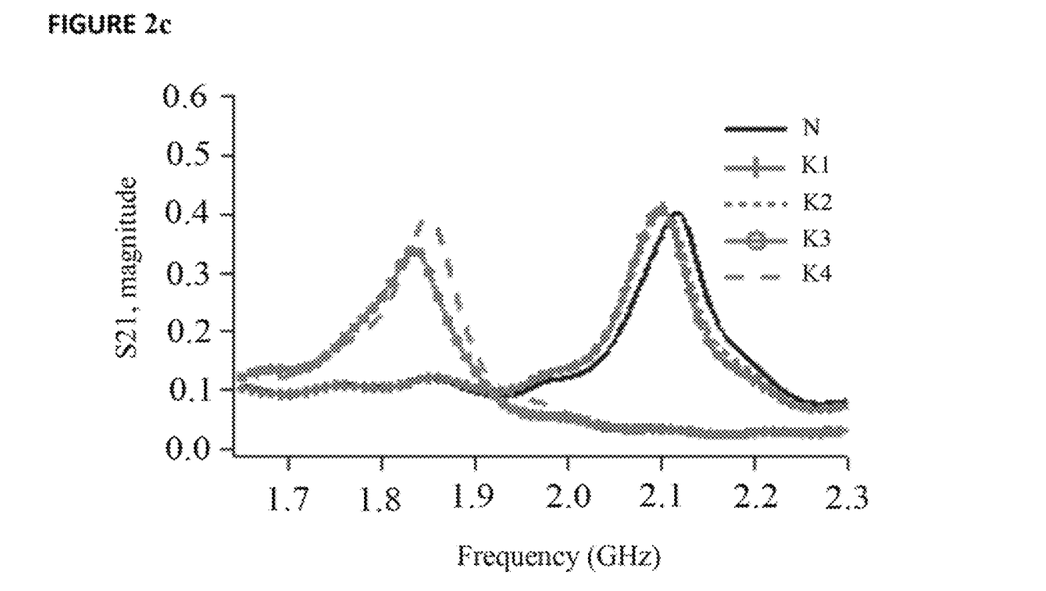
FIG. 2c is the measured transmission (s21) characteristic.

The reflection (s11) and the transmission (s21) characteristics of this experience are given in FIG. 2b. The characteristic measured when there is no droplet (L) on the biosensor (1) and called as nominal (N) created a resonant frequency with a value of 2.12 GHz. The measured reflection (s11) is high until the resonant frequency due to ground plate, and the reflection decreases sharply at the resonant frequency. The transmission (s21) is low outside of the resonant frequency where it peaks.

The resonant frequency of the metallic ring decreases due to relative permittivity increases created by the deionized water droplets (L). As a control experiment, deionized water droplets (L) were dried and measurement was repeated; and it was experimentally seen that the resonant frequency returned to the nominal value (N).

When Location—1 (K1) and Location—2 (K2) given in FIG. 2a are loaded with deionized water, because they are on the same symmetry axis, the biosensor (1) shows minimal shift in resonant frequency (1%). Since the Location—1 (K1) is present on the split ring resonator (4) gap, deionized water dropped on this point both changes the gap and surface capacitance. The dominant capacitance of the split-ring resonator (4) mentioned here is the capacitance originated from the surface loads. Larger shifts in the resonance frequency occur when the deionized water droplets (L) are placed in Location—3 (K3) and Location—4 (K) points. The change in relative frequency in this case corresponds to 14.5%. Since the biosensor (1) is reciprocal, the same results were obtained when the ports (6) of the network analyzers are interchanged. Furthermore, we should state that the electromagnetic wave emitted from the antennas (5) is not planar and the location of the antennas affects the resonant characteristic.

Biomolecular measurements were performed in order to demonstrate the use of split-ring resonator (4) based biosensor (1) as biosensor experimentally. In these measurements, the interaction between the FGF-2 (fibroblast growth factor 2, F) and heparin (H) was monitored. Specifically, prepared Murine recombinant FGF-2 (F) and low molecular weight heparin (H) molecules (Enoxaparin, Sanofi, Paris, France) were used in the experiments. FG-2 (F) is known as a molecule playing an important role in biological processes such as embryogenesis, angiogenesis and wound healing. Heparin (H) binds the FGF-2 (F) molecules through a specific domain with high affinity.

Figure 3A:
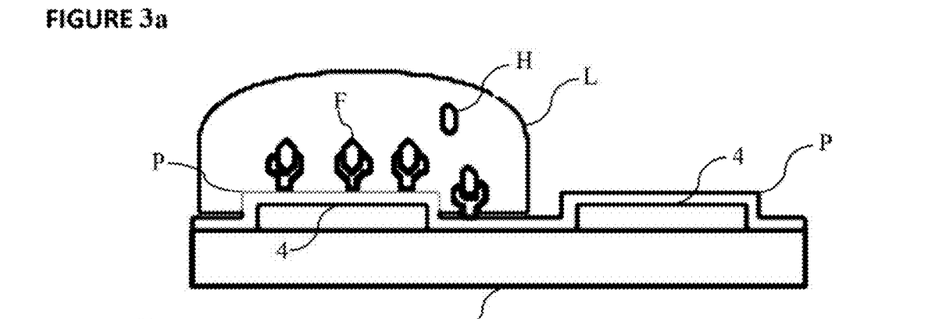
FIG. 3a is the experiment schematic showing the functionalization of biosensors with biomolecules.

The experiments started with measuring reflection (s11) and transmission (s21) spectra. The surface of the biosensor (1) coated with parylene (P) was incubated with FGF-2 (F) molecules in a certain concentration (for example 140 μg/ml). A droplet in volume of 10-μL was placed on Location—4 (K4) at room temperature, and left there for 30 minutes. Therefore, the area subjected to incubation was uniformly coated with FGF-2 (F). In the next step, the surface was dried and heparin (H) droplet in a certain volume and concentration (in volume of 20 μL, and in concentration of 10 μg/ml) was placed. The schematic of the experiment is shown in FIG. 3a. Then, the surface was dried again and this time a drop of heparin (H) molecule in volume of 20 μL and in concentration of 20 μg/ml was placed. This experimental cycle continued increasing, the heparin (H) concentration. In each step, reflection (s11) and transmission (s21) spectra were measured. The recorded spectra are given in FIG. 3b and FIG. 3c. As final step, a control experiment was performed by using deionized water with a volume of 20 μL.

Figure 3B:
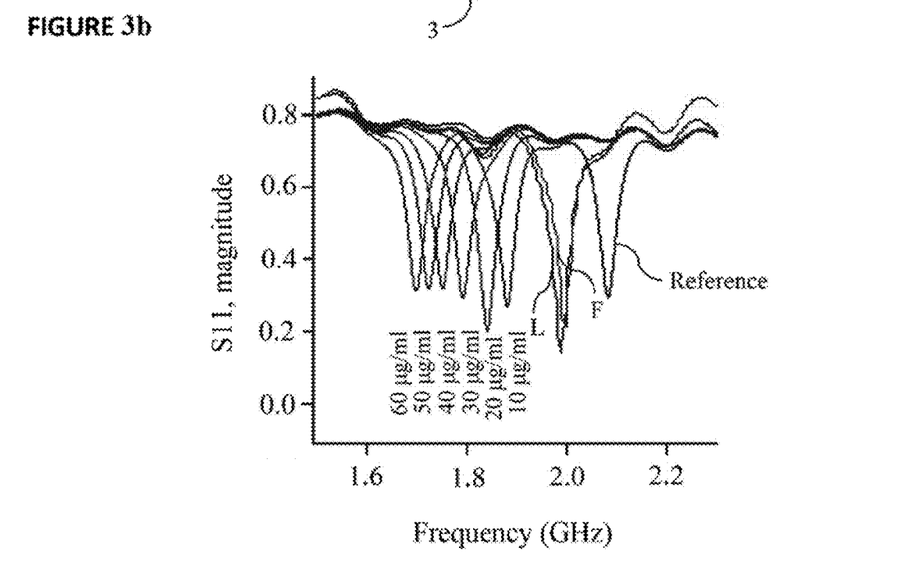
FIG. 3b is the reflection (s11) characteristic measured during experiments.
Figure 3C:
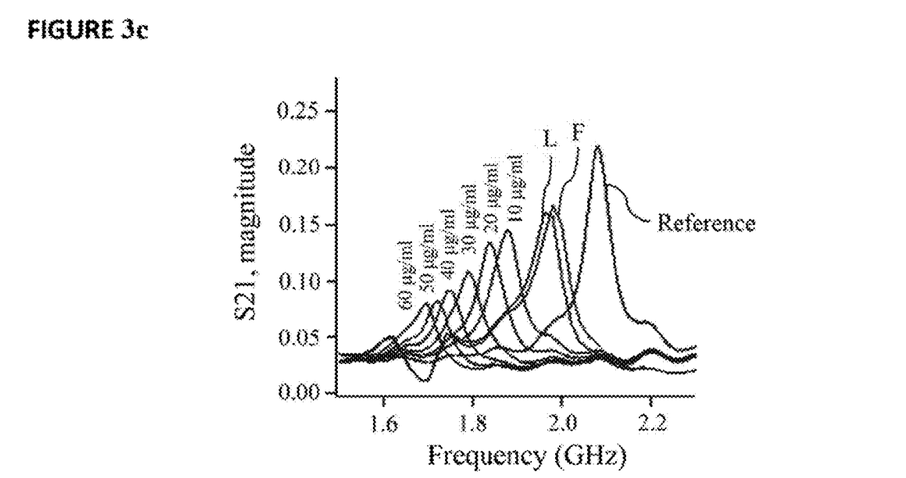
FIG. 3c is the transmission (s21) characteristic measured during experiments.

Incubation with the FGF-2 molecules in a volume of 10 μL changes the elective permittivity of the biosensor (1). The change corresponding to this situation is a 3.5% decrease in resonant frequency. Adding heparin (H) molecules caused a further decrease in resonant frequency since the increase in permittivity due to the heparin (H) molecules binding the FGF-2 molecules. Resonant frequency change measured upon adding heparin molecules in concentration of 10 μg/ml was as 10%. The decrease in resonant frequency is proportional with the increase in the molecular concentration of heparin (H). A control experiment with deionized water brought the resonant frequency to the value incubated with the FGF-2 molecules. From these results, it is evident that the effect of molecular interaction on biosensor (1) response was measured.

Figure 4:
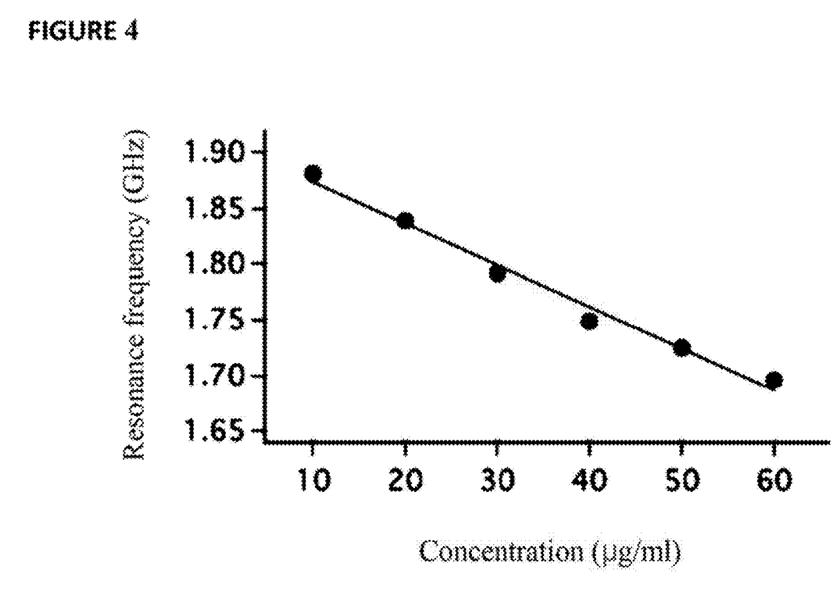
FIG. 4 is a curve showing the observed linear decrease in resonant frequency relative to heparin molecular concentration increase.

The change in resonant frequency relative to molecular concentration is given in FIG. 4. According to this graph, there is a linear dependency within measurement limits, and the sensitivity was measured as 3.7 kHz/(ng/ml). It is possible to measure interaction between molecules with sub ng/ml levels with a frequency resolution of 1 kHz at the measurement frequency band.

Using the inventive biosensor (1), in a method enabling them measurement of the transmission (s21) and reflection (s11) characteristics of split-ring resonator (4), and in order to determine the concentration of a desired molecule in a liquid in the medium the following steps are performed: first probe molecules (for example FGF-2) in a certain concentration are incubated on the surface of split-ring resonator (4) coated with a dielectric layer. In order to coat the split-ring resonator (4) area subjected to incubation with the said probe molecules (for example FGF-2) uniformly, a droplet in a certain volume is placed on a certain location on the split-ring resonator (4) at room temperature, and left for a predetermined period of time. Second, the surface of the split-ring resonator (4) is dried, and a droplet comprising a second molecule is placed (for example heparin (H)) in a certain volume and concentration. In order to measure the concentration of molecule in the said droplet, first an electric signal is applied on two symmetrical antennas (5) which are coplanar with the split-ring resonator (4). The said electric signal is converted into electromagnetic wave by the antennas (5) and transmitted to the split-ring resonator (4), and the split-ring resonator (4) is excited via the said electromagnetic waves. Then, the transmission (s21) and reflection (s11) characteristics of split-ring resonator (4) are measured using a vector network analyzer connected to the antennas (5) through ports (6) of the biosensor (1).

In order to determine the concentration of a desired molecule in a liquid in the medium, transmission (s21) and reflection (s11) characteristics of split-ring resonator before the second molecule (for example heparin (H)) is added to the medium are measured, and the obtained characteristics are compared. For this, first the abovementioned first step is performed. In first step, probe molecules in a certain concentration (for example FGF-2) are incubated on the surface of split-ring resonator (4) coated with a dielectric layer. In order to coat the split-ring resonator (4) is subjected to incubation with the said probe molecules (for example FGF-2) uniformly, a droplet in a certain volume is placed on a certain location on the split-ring resonator (4) at room temperature, and left for a predetermined period of time. An electric signal is applied on two symmetrical antennas (5) which are coplanar with the split-ring resonator (4). The said electric signal is converted into electromagnetic wave by the antennas (5) and transmitted to the split-ring resonator (4), and the split-ring resonator (4) is excited via the said electromagnetic waves. Then, the transmission (s21) and reflection (s11) characteristics of split-ring resonator (4) are measured with a vector network analyzer. The measured characteristic is considered as a reference.

These reference characteristic values which are obtained are compared with the transmission (s21) and reflection (s11) characteristics of the split-ring resonator (4) after the second molecule is added to the medium. By referencing the shift in resonant frequency due to the second molecule added to the medium (which are towards lower frequencies), the concentration of the second molecule in the medium (for example heparin (H)) is determined easily. This process is determined considering the characteristic values, which are recorded before in one embodiment of the invention. In another embodiment of the invention the concentration value of the second molecule in the medium is determined by calculating the shift in resonant frequency with respect to a control unit and comparing with pre-recorded data.

The invention claimed is:

1. A method which enables determining a concentration of a desired molecule inside a liquid medium by using a biosensor,
    wherein the biosensor, which enables measuring the concentration of a desired molecule inside a liquid medium, comprises:
    at least one metallic plate which functions as a ground plate, and is manufactured from aluminum;
    at least one dielectric substrate which is located on top of the at least one metallic plate; and
    at least one split-ring resonator which is realized on top of the at least one dielectric substrate,
    and characterized by
    at least two symmetrical antennas which are realized on the same plane with the at least one split-ring resonator on top of the at least one dielectric substrate and which are exciting the at least one split-ring resonator by emitting electromagnetic waves,
    the at least one metallic plate enables the electromagnetic waves emitted from the at least two symmetrical antennas to be transmitted to the at least one split-ring resonator by reflecting the electromagnetic waves,
    at least two ports where a network analyzer is connected to the at least two symmetrical antennas,
    wherein the method is characterized by the steps of
    incubating probe molecules in a certain concentration on a surface of the at least one split-ring resonator coated with a dielectric layer,
    placing a droplet in a certain volume on a certain location on the at least one split-ring resonator at room temperature, and waiting for a determined time in order to coat an area subjected to incubation with the probe molecules uniformly,
    applying an electric signal on the at least two symmetrical antennas which are coplanar with the at least one split-ring resonator,
    converting the electric signal to electromagnetic wave by the at least two symmetrical antennas and exciting the at least one split-ring resonator,
    measuring transmission and reflection characteristics of the at least one split-ring resonator with a vector network analyzer,
    drying the surface, placing a droplet comprising a second molecule in a certain volume and concentration, applying an electric signal on the at least two symmetrical antennas which are coplanar with the at least one split-ring resonator,
    converting the electric signal to electromagnetic wave by the at least two symmetrical antennas and exciting the at least one split-ring resonator,
    measuring the transmission and reflection characteristics of the at least one split-ring resonator again with a vector network analyzer,
    comparing the transmission and reflection characteristics of the at least one split-ring resonator which are measured to reference measurements, and thus determining the concentration of the second molecule.

2. The method according to claim 1, wherein the reference measurements are obtained by
    a) incubating probe molecules in a certain concentration on the surface of the at least one split-ring resonator coated with a dielectric layer,
    b) placing a droplet in a certain volume on a certain location on the at least one split-ring resonator at room temperature, and waiting for a determined time in order to coat the area subjected to incubation with the probe molecules uniformly,
    c) drying the area, placing a droplet comprising a second molecule in a certain volume with a certain concentration, applying an electric signal on the at least two symmetrical antennas which are coplanar with the at least one split-ring resonator,
    d) converting the electric signal to an electromagnetic wave by the at least two symmetrical antennas and exciting the at least one split-ring resonator,
    e) measuring transmission and reflection characteristics of the at least one split-ring resonator again with a vector network analyzer and recording the transmission and reflection characteristics of the at least one split-ring resonator as data.

* * * * *